US008682584B2

(12) United States Patent
Baker et al.

(10) Patent No.: US 8,682,584 B2
(45) Date of Patent: Mar. 25, 2014

(54) NITROGEN POTENTIAL INDEX

(75) Inventors: Luke Baker, New Knoxville, OH (US); Thomas Menke, Greenville, OH (US)

(73) Assignee: Brookside Laboratories, Inc., New Knoxville, OH (US)

( * ) Notice: Subject to any disclaimer, the term of this patent is extended or adjusted under 35 U.S.C. 154(b) by 392 days.

(21) Appl. No.: 13/213,468

(22) Filed: Aug. 19, 2011

(65) Prior Publication Data

US 2013/0046468 A1 Feb. 21, 2013

(51) Int. Cl.
*G06F 19/00* (2011.01)

(52) U.S. Cl.
USPC .... 702/2; 405/128.75; 405/128.7; 405/128.5; 405/129.1; 435/262.5; 800/278; 71/11; 71/28

(58) Field of Classification Search
USPC ............. 702/2; 405/302.4, 15, 128.75, 128.7, 405/128.5, 129.85, 129.95, 129.57, 128.1, 405/128.45, 129.1; 435/262.5, 320.1, 7.92, 435/412, 468; 800/276, 278, 287; 71/1, 6, 71/11, 28, 30; 166/294, 305.1, 256, 302, 166/261, 272.1, 402, 250.01, 245, 272.7
See application file for complete search history.

(56) References Cited

U.S. PATENT DOCUMENTS

| | | | | |
|---|---|---|---|---|
| 4,997,469 A * | 3/1991 | Moore | | 71/11 |
| 5,039,328 A * | 8/1991 | Saitoh et al. | | 71/28 |
| 6,699,709 B1 * | 3/2004 | Bonde et al. | | 435/262.5 |
| 6,936,573 B2 * | 8/2005 | Wertz et al. | | 504/367 |
| 7,030,287 B2 * | 4/2006 | Murasawa et al. | | 210/610 |
| 7,841,806 B2 * | 11/2010 | Lindenbaum | | 405/302.4 |
| 8,012,912 B1 * | 9/2011 | Barrick et al. | | 504/165 |
| 8,092,118 B2 * | 1/2012 | Atkin et al. | | 405/129.1 |
| 8,491,858 B2 * | 7/2013 | Seeker et al. | | 423/105 |
| 2004/0023809 A1 * | 2/2004 | Wertz et al. | | 504/360 |
| 2005/0158871 A1 * | 7/2005 | Ro et al. | | 436/173 |
| 2005/0178724 A1 * | 8/2005 | Murasawa et al. | | 210/605 |
| 2007/0095118 A1 * | 5/2007 | Evers et al. | | 71/28 |
| 2009/0293147 A1 * | 11/2009 | Dhugga et al. | | 800/278 |
| 2012/0014748 A1 * | 1/2012 | Kubota et al. | | 405/128.7 |

FOREIGN PATENT DOCUMENTS

RU 2249937 C2 * 4/2005

OTHER PUBLICATIONS

Anderson et al., "Using the Nitrogen Mineralization Soil Test to Predict Spring Fertilizer N Rate", Oregon State University, EM9020, pp. 1-5, Nov. 2010.

Thomas Appel, "Relevance of soil N mineralization, total N demand of crops and efficiency of applied N for fertilizer recommendations for cereals—Theory and application", Wiley online library, Abstract, Jan. 12, 2007.

(Continued)

*Primary Examiner* — Carol S Tsai
(74) *Attorney, Agent, or Firm* — Dinsmore & Shohl LLP

(57) ABSTRACT

Embodiments of a method for assessing potential nitrogen concentration of plant available nitrogen in soil comprises collecting soil samples, analyzing one or more of the soil samples to compute the amount of nitrate and the amount of ammonium, analyzing one or more of the soil samples to compute the amount of mineralizable nitrogen using a soil respiration method, obtaining a total plant available nitrogen value in the soil samples by summing the computed nitrate value, the computed ammonium value, and the computed mineralizable nitrogen value, and calculating a potential nitrogen assessment value by subtracting from the total plant available nitrogen value an amount of nitrogen applied at time of planting not represented within the soil sample and further subtracting an amount of nitrogen required to achieve the crop yield goal multiplied by the yield crop goal.

11 Claims, 1 Drawing Sheet

(56) References Cited

OTHER PUBLICATIONS

Balkcom et al., "Measuring Soil Nitrogen Mineralization under Field Conditions", Communications in Soil Science and Plant Analysis, 40, pp. 1073-1086, 2009.

Dinnes et al., "Plant-Soil-Microbe N Relationships in High Residue Management Systems", South Dakota No Till Association Annual Conference, Jan. 25, 2001.

Franzluebbers et al., "Soil Nitrogen Mineralization Potential for Improved Fertilizer Recommendations and Decreased Nitrate Contamination of Groundwater", Texas Water Resources Institute, Sep. 1995.

Haney et al., "Estimating Soil Carbon, Nitrogen, and Phosphorus Mineralization from Short-Term Carbon Dioxide Respiration", Communiations in Soil Science and Plan Analysis, 39, pp. 2706-2720, 2008.

Haney et al., "Soil CO2 respiration: Comparison of Chemical titration, CO2 IRGA analysis and the Solvita gel system", Cambridge Journals Online—vol. 23, Issue 2, Abstract, 2008.

Kryzanowski et al., "Nitrogen Mineralization Estimate for Alberta Soils", Alberta Agriculture, Food & Rural Development, 2006.

May et al., "Soil Testing to Optimize Nitrogen Management for Processing Tomatoes", California Department of Food and Agriculture, Aug. 17, 2001.

J.J. Neeteson, "Development of nitrogen fertilizer recommendations for arable crops in the Netherlands in relating to nitrate leaching", Fertilizer Research 26, pp. 291-298, 1990.

Sullivan et al., "Worksheet for Calculating Biosolids Application Rates in Agriculture", Oregon State University, Mar. 1999.

Water Environment Research Foundation, "Calculating Biosolids Application Rates for Agriculture, Appendix A", Oregon State Unifersity, Mar. 1999.

Darryl Warncke, "Soil nitrate test for corn in Michigan", Crop and Soil Sciences, May 14, 2009.

* cited by examiner

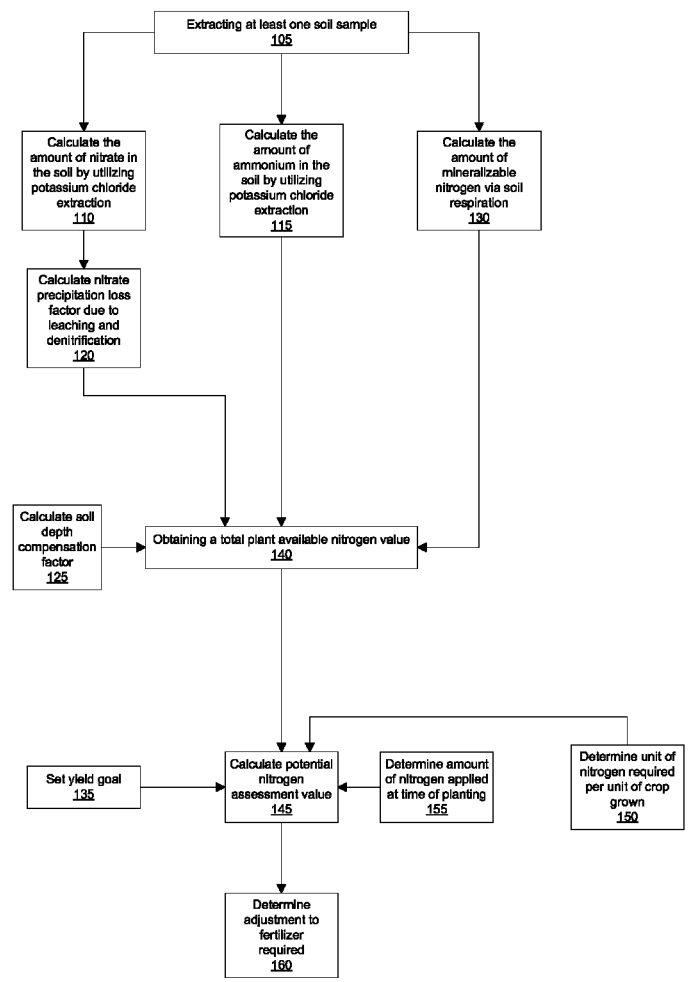

NITROGEN POTENTIAL INDEX

BACKGROUND

The present invention is generally directed to soil analysis, and is specifically directed to embodiments of analyzing the nitrogen potential in soil samples. Determining the amount of plant available nitrogen is a continual challenge for crop producers. Based on this uncertainty, the crop producer is often led to speculate how much supplementary fertilizer is required to achieve the desired crop yield.

SUMMARY

Embodiments of the present invention eliminate this guesswork for the crop producer via the presently disclosed comprehensive methodology that informs the crop producer of the amount of nitrogen in the soil, the potential nitrogen concentration in the compost or soil, and the amount of supplementary fertilizer required to achieve a desired crop yield goal.

According to one embodiment, a method for assessing potential nitrogen concentration of plant available nitrogen in soil is provided. The method comprises collecting soil samples, analyzing one or more of the soil samples to compute the amount of nitrate and the amount of ammonium, analyzing one or more of the soil samples to compute the amount of mineralizable nitrogen using a soil respiration method, obtaining a total plant available nitrogen value in the soil samples by summing the computed nitrate value, the computed ammonium value, and the computed mineralizable nitrogen value, and calculating a potential nitrogen assessment value by subtracting from the total plant available nitrogen value an amount of nitrogen applied at time of planting not represented within the soil sample and further subtracting an amount of nitrogen required to achieve the crop yield goal multiplied by the yield crop goal.

These and additional objects and advantages provided by the embodiments of the present invention will be more fully understood in view of the following detailed description, in conjunction with the drawings.

BRIEF DESCRIPTION OF THE DRAWINGS

The following detailed description of specific embodiments of the present invention can be best understood when read in conjunction with the drawings enclosed herewith.

FIG. 1 is a flow chart depicting the process for obtaining the nitrogen potential index, according to one or more embodiments of the present invention.

The embodiments set forth in the drawings are illustrative in nature and not intended to be limiting of the invention defined by the claims. Moreover, individual features of the drawings and invention will be more fully apparent and understood in view of the detailed description.

DETAILED DESCRIPTION

Embodiments of the present disclosure are directed to a method for assessing potential nitrogen concentration of plant available nitrogen in soil. While the present examples and methodology describe the amount of nitrogen used to produce corn crops, various soils and various types of crop production are applicable to the present methodology. Moreover, the present methodology would improve the crop yield and the predictability of the crop yield for all types of soils and crops.

The potential nitrogen assessment (PNA) value is an index value that provides the amount of supplemental nitrogen requirements necessary to achieve a crop yield. The presently described methodology described below achieves a comprehensive value that instructs the user of the amount of nitrogen needed to achieve a desired crop yield, and also provides insight regarding the nitrogen capacity of the soil or composts prior to supplementation.

Referring to the embodiment of FIG. 1, embodiments of a method for assessing potential nitrogen concentrations of plant available nitrogen in soil are provided. The method comprises a step of collection one or more soil samples 105. As used herein, the soil samples may comprise one or multiple soil specimens. For example, it is possible that one sample may be used for analysis of the amount of nitrate, ammonium, and potentially mineralizable nitrogen, or it is possible that three separate samples may be used to analyze the amount of nitrate, ammonium, and potentially mineralizable nitrogen.

Upon collection, the soil samples may be analyzed to compute the amount of nitrate and the amount of ammonium in the soil samples. Various methods are contemplated for the extraction and analysis of the nitrate and ammonium. For example and not by way of limitation, the amount of nitrate and/or ammonium in the soil sample may first be analyzed and computed via potassium chloride extraction 110. While various procedures are contemplated for the potassium chloride extraction, one such exemplary potassium chloride extraction procedure is detailed in Mulvaney et al article, *Nitrogen—inorganic forms*, Methods of soil analysis. Part 3—chemical methods. 1996 pp. 1123-1184, which is incorporated by reference herein in its entirety.

As stated above, while various modifications to the procedure are contemplated, the potassium chloride extraction procedure primarily utilizes the steps of adding a potassium chloride extractant, allowing the soil and extractant mix for a period, for example, at least 15-30 minutes, filter the product, and analyze the nitrate and ammonium present utilizing a color measurement spectrophotometer. The Mulvaney method provides potassium chloride via two steps. For example, in Mulvaney, the soil sample is treated with a mixture of KOBr and KOH before extraction with HF—HCl. With this procedure, it is easier to determine the amount of exchangeable and non-exchangeable ammonium and nitrates inside the soil extracted from the filtering step. As would be familiar to one of ordinary skill in the art, the amount of ammonium and nitrate is computed based on the colorimetric reading provided by the spectrophotometer.

Various other methods are contemplated for the extraction and analysis of nitrate and ammonium. Alternatively, the computation of the amount of ammonium and nitrate may be performed using steam-distillation methods, microdiffusion methods, colorimetric methods, and methods using ion-selective electrodes, or combinations thereof.

After obtaining the values for the amount of nitrate or ammonium, it may be beneficial to compensate for environmental conditions. Without being bound by theory, nitrate losses in the soil may result from environmental conditions. Nitrate values computed in the potassium chloride extraction procedure assume ideal conditions; however, obtaining ideal environmental conditions is not always possible. For example, nitrate losses in the soil may occur due to various environmental conditions, for example, leeching or denitrification of the soil. Leeching may be caused by various weather related factors. For example, leaching results when heavy rainfall carries away some of the soil and forms a dense bottom layer. By stripping away portions of the top layer, at least a portion of the beneficial nitrogen in the top layer is stripped away. In contrast, denitrification is the formation of denitrifying bacteria in standing or stagnant water that removes nitrogen from the soil. With proper irrigation, denitrification may be minimized.

Consequently, when calculating the compensation value for the loss of nitrate or ammonium, one major consideration is the soil type. For example, denitrification is a more significant issue for thicker silt and clay soils, because irrigation is more challenging, and thus standing water is more likely. On the converse, leeching is less likely for thicker silt and clay soils, as rainfall is less likely to carry way a top layer of thicker soil. For example and not by way of limitation, denitrification may decrease the amount of nitrate by about 25 to about 50% in the soil. Alternatively, there is very little if any denitrification in sandy soils, because draining is more effective for sandy soils. However, leeching is more prevalent for sandy soils, because rainfall is highly effective at stripping away the top layer of sandy soil. For example and not by way of limitation, leeching may remove about 70% or more of nitrate in a sandy soil sample due to leeching.

As would be understood, the compensation for the nitrate values also considers the climate as well as any mechanisms for compensation of leaching and denitrification in the soil. For example, the amount of rainfall is considered, especially in sandy soils. Alternatively, the sophistication of the drainage system is also contemplated when considering the nitrate losses. Various mechanisms are utilized for computing this loss factor for the nitrate. For example, the loss factor may be computed from a lookup table that provides a percentage loss factor as described above for the final set of results. For example and not by way of limitation, an exemplary lookup is provided below.

TABLE 1

| # of Days Saturated | Average Temperature (° F.) | | | |
|---|---|---|---|---|
| | <32° F. | 32 to 50° F. | 50 to 60° F. | >60° F. |
| | % of Nitrate Nitrogen Lost | | | |
| <3 | 0 | 0 | 0 | 0 |
| 4 to 5 | 0 | 5 | 20 | 40 |
| 6 to 7 | 0 | 10 | 30 | 50 |
| 8 to 10 | 0 | 15 | 40 | 60 |
| >10 | 0 | 20 | 60 | 80 |

In further examples, the denitrification/leaching factors may be computed as follows: If soils are saturated for 4 to 7 days then we decrease the nitrate reported by 25%, if soils are saturated >7 days then we decrease the nitrate reported by 50%, and in sandy soils after a heavy rainfall event (4 to 6 inches of rain within five days) we decrease nitrate reported by 70% due to leaching losses.

While nitrogen losses are more prevalent, it is contemplated that there could be some amount of loss of ammonium in the soil due to environmental factors; however, the ammonium losses are typically negligible. As ammonium is a positively charged element, it is converted into nitrate, and the converted nitrate is removed via leaching or denitrification; however, the leaching or denitrification of ammonium is unlikely. After determining the amount of ammonium and the compensated value for the nitrate, these values may be utilized in the computation of the total plant available nitrogen.

In addition to calculating the amount of ammonium and nitrate, it is essential to also calculate the mineralizable nitrogen. Referring to FIG. 1, the embodiments of the present invention may analyze soil samples to compute the amount of mineralizable nitrogen. Various methods for determining the amount of mineralizable nitrogen in the soil sample are contemplated herein, for example, the methodologies described above for the calculation of ammonium and nitrate. One exemplary embodiment for computing the mineralizable nitrogen is a soil respiration method 130 (also called $CO_2$ respiration). Whereas various soil respiration procedures are contemplated as suitable, specific embodiments may utilize the soil respiration method disclosed in Haney et al, *Estimating Soil Carbon, Nitrogen, and Phosphorus Mineralization from Short-Term Carbon Dioxide*, Communications in Soil Science and Plant Analysis, 39: 2706-2720, 2008, which is incorporated by reference herein in its entirety.

The Haney method, which is utilized by Solvita, quantifies the relative differences in $CO_2$ respiration to determine the mineralizable nitrogen. When measuring the $CO_2$ evolution from compost or soil, a pH-sensitive gel (paddle) is inserted into the compost. After a suitable time-period (for example, a time ranging from 5 minutes to 5 days), the paddle is removed from the compost and analyzed visually or optionally with a digital reader. The absorbed $CO_2$ on the paddle produces a colorimetric reaction that is either visually compared to a color key or automatically read via a digital color reader (DCR).

In addition to compensating for environmental factors as described above, the method may also account for the sampling depth, since not all users sample to the same depth. Since some users may sample to 8 inches whereas other users may sample to 12 inches, the method may utilize a correction factor to normalize all sample amounts. Regarding nitrate, a 12 inch sample for nitrate is equivalent to an 8 inch sample. Thus, a compensation factor is included to ensure that the producer accounts for the nitrate in the next 4 inches of soil when using an 8 inch sample, which causes greater nitrogen fertilizer recommendations. While not being bound by theory, nitrates are subject to loss from the soil due to moisture, temperature and time, whereas other forms or nitrogen are relatively stable.

After computing the amount of mineralizable nitrogen, the method may include the step of determining the total plant available nitrogen value 140 in the soil by summing the computed nitrate value, the computed ammonium value, and the computed mineralizable nitrogen value. After calculating the total plant available nitrogen, the method may include the step of calculating the potential nitrogen assessment value (PNA). To perform the calculation, the following other variables may be considered: 1) the amount of nitrogen applied at time of planting not represented within the sample (k) To determine this amount, soil samples are generally collected prior to addition of fertilizer or the samples may be collected in an unfertilized region. It may be sampled after fertilizer addition as well. For example, if fertilizer has been added, the test should pick it up unless it is banded in the row at planting time and sampling protocol avoids that area. Beneficially, this test enables producers to sample much earlier in the season before crops are planted or right at planting so that they can side dress nitrogen without having to wait on a result from the lab; 2) the amount of nitrogen required to achieve the crop yield goal (i); and 3) amount of nitrogen required per unit of the crop (j).

The amount of nitrogen required to achieve the crop yield goal may be calculated by multiplying a yield goal of the crop and an amount of nitrogen per unit of the crop. The yield goal of the corn crop to be grown (in bushels per acre or kilograms per hectare) is determined by the crop producer. Certain soil has the ability to produce different yields based on its chemical, physical, and biological properties. Based on experience and these variables, the crop producer may determine how much crop can be produced. Moreover, the yield goal may also determined by historical records of the field and the demonstrated genetic potential of the crop.

The amount or unit of nitrogen required per unit of crop grown (typically in pounds per bushel or gram per kilogram) is a well known parameter familiar to one of ordinary skill in the art. As would be familiar to the person skilled in the art, this value, which may be gleaned from literature, varies. For example, the amount of nitrogen per unit of crop grown may vary from about 1.2 to about 1.7 pounds of nitrogen per bushel of yield. This value includes the amount of N needed to grow a bushel of corn, which also includes stover (leaves and stems) and roots. Recommendations that only include the amount of nitrogen needed to produce the grain and forget about the other parts of the plant are not comprehensive. Alternatively, the value may be obtained experimentally by testing one or more different portions of the plant for nitrogen content and weighing them to extrapolate a per acre or per hectare basis.

Utilizing these variables, the potential nitrogen assessment value (PNA) is calculated by subtracting from the total plant available nitrogen value a the amount of nitrogen applied at time of planting k and further subtracting the amount of nitrogen required to achieve the crop yield goal j multiplied by the yield goal i. The computations may be performed manually or may be performed via a processor which executes a computer algorithm or program.

Optionally, the user may compute an amount of additional fertilizer required based on the calculated potential nitrogen assessment (PNA) value and the crop yield goal (i×j). By using the formula below, if we have a yield goal and an estimate for the amount of N the crop will need we can estimate N needs. Next, we we measure the ammonium, nitrate, and mineralizable N fraction and add these together with some depth and rainfall adjustments to compute the PNA index. By subtracting the two numbers, we can obtain the additional N needed, As would be familiar to one of ordinary skill in the art, the nitrogen includes broadcast and band applied nitrogen fertilizer sources. As used herein, "broadcast" means scattered fertilizer, for example, randomly scattered fertilizer. As used herein, "band applied" means a more evenly or uniformly applied fertilizer.

Attached is a sample table showing the potential nitrogen assessment index for different corn yields and the amount of potential nitrogen needed per acre.

To calculate the amount of plant available nitrogen a, the following equation is used $$a = [b \times (1-c) \times d \times (e/3)] + [f \times (e/3)] + [g \times (e/3)]$$

The variable a is the total available nitrogen from the sample (in pounds per acre or kilograms per hectare); b is the total amount of nitrate extracted from the soil sample (in pounds per acre or kilograms per hectare), c is a precipitation loss factor, d is the nitrate soil compensation factor, e is the depth of the soil sample submitted in inches (or metric equivalent), f is the total amount of ammonium nitrogen (in pounds per acre or kilograms per hectare); and g is the total amount of mineralizable nitrogen (in pounds per acre or kilograms per hectare).

The potential nitrogen assessment (PNA) value may be determined with the following equation by utilizing the computed total available nitrogen a:

$$PNA = a - (i \times j) - k$$

wherein i is the yield goal of the crop to be grown (in bushels per acre or kilograms per hectare), j is the unit of nitrogen required per unit of crop grown (in pounds per bushel or gram per kilogram), and k is the amount of nitrogen applied at the time of planting (in pounds per acre or kilograms per hectare).

Prophetic Example 1

1) Soil Collection: 10 to 15 soil sample are collected to a depth of 8 to 12 inches 2) Computation of ammonium and nitrate via potassium chloride extraction: The yielded ammonium value is 4 ppm, and the computed nitrate is 15 ppm. For the nitrate calculation, the unadjusted nitrate was 20 ppm, the nitrate precipitation loss was computed from the above lookup table as being 40% (above 60° F. and 4-5 days saturation), and the nitrate soil compensation factor is 1.25. Using the above equation, the calculation is 20*(1-0.4)*1.25=15 ppm.

3) Computation of mineralizable nitrogen via soil respiration: This is determined using the Solvita system described above. The yielded value is multiplied by a depth factor to get pounds per acre. For example, 35 parts per million of mineralizable nitrogen sampled to a depth of 8 inches would result in 35*(8/3)=93.3 pounds per acre of mineralizable nitrogen. Note: To calculate pounds per acre from parts per million you take the sample depth divided by 3. This is related to

TABLE 2

| | Potential Nitrogen Assessment Index (PNA) | | | | | | | | | | | | | |
|---|---|---|---|---|---|---|---|---|---|---|---|---|---|---|
| Corn Yield (bu/a) | 50 | 70 | 90 | 110 | 130 | 150 | 170 | 190 | 210 | 230 | 250 | 270 | 290 | 310 |
| | Pounds of Additional Nitrogen Needed per acre | | | | | | | | | | | | | |
| 120 | 148 | 128 | 108 | 88 | 68 | 48 | 28 | 8 | 0 | 0 | 0 | 0 | 0 | 0 |
| 130 | 165 | 145 | 125 | 105 | 85 | 65 | 45 | 25 | 0 | 0 | 0 | 0 | 0 | 0 |
| 140 | 181 | 161 | 141 | 121 | 101 | 81 | 61 | 41 | 21 | 0 | 0 | 0 | 0 | 0 |
| 150 | 198 | 178 | 158 | 138 | 118 | 98 | 78 | 58 | 38 | 18 | 0 | 0 | 0 | 0 |
| 160 | 214 | 194 | 174 | 154 | 134 | 114 | 94 | 74 | 54 | 34 | 14 | 0 | 0 | 0 |
| 170 | 231 | 211 | 191 | 171 | 151 | 131 | 111 | 91 | 71 | 51 | 31 | 11 | 0 | 0 |
| 180 | 247 | 227 | 207 | 187 | 167 | 147 | 127 | 107 | 87 | 67 | 47 | 27 | 7 | 0 |
| 190 | 264 | 244 | 224 | 204 | 184 | 164 | 144 | 124 | 104 | 84 | 64 | 44 | 24 | 0 |
| 200 | 280 | 260 | 240 | 220 | 200 | 180 | 160 | 140 | 120 | 100 | 80 | 60 | 40 | 20 |
| 210 | 297 | 277 | 257 | 237 | 217 | 197 | 177 | 157 | 137 | 117 | 97 | 77 | 57 | 37 |
| 220 | 313 | 293 | 273 | 253 | 233 | 213 | 193 | 173 | 153 | 133 | 113 | 93 | 73 | 53 |

For example, and not by way of limitation, utilizing the above described variables, the PNA index number and additional required fertilizer may be calculated using the following exemplary formula. The following calculation shows the means of calculating the PNA index number and the amount of nitrogen needed per acre.

2,000,000 pounds of soil in a 6 inch sample, so there would be 4,000,000 pounds of soil in a 12 inch sample. For a 12 inch sample depth then 35*(12/3)=140 pounds of mineralizable nitrogen per acre.

4) Computation of plant available nitrogen: For a 12 inch sample that had 35 ppm of mineralizable nitrogen, an ammonium value of 4 ppm, and a nitrate value of 15 parts per million would yield: 35*(12/3)+4*(12/3)+15*(12/3)=216 pounds of plant available N per acre.

5) Computation of potential nitrogen assessment value and the amount of supplementary fertilizer needed: If our yield goal is 180 bushels per acre of corn and we know that each bushel of corn removes 1.69 pounds of N per bushel produced, the computed pounds of N needed to produce 180 bushels per acre is 1.69*180=302.4. As it was computed that we had 216 pounds of plant available N per acre (302.4−216)=86.4 pounds of additional nitrogen is needed as fertilizer to produce 180 bushel per acre corn.

It is further noted that terms like "preferably," "generally," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for assessing potential nitrogen concentration of plant available nitrogen in soil comprising:

collecting soil samples;

analyzing one or more of the soil samples to compute the amount of nitrate and the amount of ammonium;

analyzing one or more of the soil samples to compute the amount of mineralizable nitrogen using a soil respiration method;

obtaining a total plant available nitrogen value in the soil samples by summing the computed nitrate value, the computed ammonium value, and the computed mineralizable nitrogen value; and calculating a potential nitrogen assessment value by subtracting from the total plant available nitrogen value an amount of nitrogen applied at time of planting not represented within the soil sample and further subtracting an amount of nitrogen required to achieve the crop yield goal multiplied by the yield crop goal.

2. The method of claim 1 further comprising optionally computing an amount of additional fertilizer required based on the calculated potential nitrogen assessment value and the crop yield.

3. The method of claim 1 wherein the amount of nitrate in the soil sample is analyzed and computed via potassium chloride extraction.

4. The method of claim 1 wherein the amount of ammonium in the soil sample is analyzed and computed via potassium chloride extraction.

5. The method of claim 1 wherein the amount of nitrogen required to achieve the crop yield goal is calculated by multiplying a yield goal of the crop and an amount of nitrogen per unit of the crop.

6. The method of claim 1 wherein the nitrogen includes broadcast and band applied nitrogen fertilizer sources.

7. The method of claim 1 wherein the computation of the amount of ammonium and nitrate is performed using steam-distillation methods, microdiffusion methods, colorimetric methods, and methods using ion-selective electrodes, potassium chloride extraction, or combinations thereof.

8. The method of claim 1 further comprising predicting nitrate losses due to the soil due to leeching or denitrification of the soil, and thereby computing a predicted nitrate loss value.

9. The method of claim 8 further comprising utilizing the predicted nitrate loss value to adjust the computed amount of nitrate in the soil sample.

10. The method of claim 1 further comprising computing the depth of the soil sample.

11. The method of claim 10 further comprising compensating for the depth of the soil sample using a soil compensation factor.

* * * * *